United States Patent
Clark et al.

(10) Patent No.: US 7,330,583 B2
(45) Date of Patent: Feb. 12, 2008

(54) INTEGRATED VISUAL IMAGING AND ELECTRONIC SENSING INSPECTION SYSTEMS

(75) Inventors: Bernard T. Clark, Los Gatos, CA (US); David L. Freeman, Los Gatos, CA (US); Jeffrey A. Hawthorne, Unionville (CA); Alexander J. Nagy, Santa Cruz, CA (US); William K. Pratt, Los Altos, CA (US)

(73) Assignee: Photon Dynamics, Inc., San Jose, CA (US)

( * ) Notice: Subject to any disclaimer, the term of this patent is extended or adjusted under 35 U.S.C. 154(b) by 644 days.

(21) Appl. No.: 10/223,288

(22) Filed: Aug. 19, 2002

(65) Prior Publication Data

US 2004/0032280 A1    Feb. 19, 2004

(51) Int. Cl.
*G06K 9/00* (2006.01)
(52) U.S. Cl. ............ 382/149; 250/443.1; 250/559.08; 250/559.46; 324/770; 382/152
(58) Field of Classification Search ............ 250/443.1, 250/492.1, 559.08, 559.46; 324/753, 770, 324/751; 374/5, 142; 382/149, 144, 145, 382/152, 147
See application file for complete search history.

(56) References Cited

U.S. PATENT DOCUMENTS

| | | | |
|---|---|---|---|
| 4,843,312 A | 6/1989 | Hartman et al. | |
| 4,983,911 A | 1/1991 | Henley | |
| 5,081,687 A | 1/1992 | Henley et al. | |
| 5,363,037 A | 11/1994 | Henley et al. | |
| 5,459,410 A * | 10/1995 | Henley | 324/770 |
| 5,689,341 A | 11/1997 | Hayashi | |
| 5,734,158 A | 3/1998 | Nagashima et al. | |
| 5,740,352 A | 4/1998 | Philipp et al. | |
| 5,793,221 A | 8/1998 | Aoki | |
| 5,872,610 A | 2/1999 | Kobayashi | |
| 5,933,028 A | 8/1999 | Kushiyama | |
| 5,994,916 A | 11/1999 | Hayashi | |
| 5,999,012 A * | 12/1999 | Listwan | 324/770 |
| 6,104,449 A | 8/2000 | Takahashi et al. | |
| 6,111,424 A * | 8/2000 | Bosacchi | 324/770 |
| 6,178,246 B1 * | 1/2001 | Bebesel et al. | 381/71.2 |

(Continued)

FOREIGN PATENT DOCUMENTS

JP     06-174921     6/1994

(Continued)

*Primary Examiner*—Gregory Desire
(74) *Attorney, Agent, or Firm*—Blakely Sokoloff Taylor & Zafman LLP (57) ABSTRACT

Integrated inspection and test systems for liquid crystal display (LCD) active plates. The integrated inspection and test systems may combine visual imaging inspection and an electronic sensing such as voltage imaging, electron beam sensing or charge sensing, in which the potential defect information obtained by the visual inspection system is combined with the potential defect information obtained by the electronic sensing system to produce a defect report. One or more high-resolution visual cameras are scanned over a stationary plate, and the image data from the camera(s) is processed to detect potential defects. A high-resolution electronic sensing system examines the stationary plate, and the image data from the sensor(s) is processed to detect potential defects. The potential defects from the visual image data and electronic sensing image data are processed to produce the final defect information.

22 Claims, 4 Drawing Sheets

U.S. PATENT DOCUMENTS

| | | |
|---|---|---|
| 6,232,616 B1 | 5/2001 | Chen et al. |
| 6,272,204 B1 | 8/2001 | Amtower et al. |
| 6,285,207 B1 * | 9/2001 | Listwan .................. 324/770 |
| 6,696,692 B1 * | 2/2004 | Pepper ................. 250/492.21 |
| 6,840,666 B2 * | 1/2005 | Enachescu et al. ............ 374/5 |
| 7,095,883 B2 * | 8/2006 | Safaee-Rad et al. ........ 382/141 |
| 7,116,398 B2 * | 10/2006 | Hoefnagels et al. .......... 355/52 |
| 2004/0032280 A1 * | 2/2004 | Clark et al. ................. 324/770 |

FOREIGN PATENT DOCUMENTS

| | | |
|---|---|---|
| TW | 354834 | 3/1999 |
| TW | 448328 B | 8/2001 |
| TW | 487820 B | 5/2002 |

* cited by examiner

VISIBLE LIGHT AND CHARGE SENSING

FIG. 7

INTEGRATED VISUAL IMAGING AND ELECTRONIC SENSING INSPECTION SYSTEMS

BACKGROUND OF THE INVENTION

1. Field of the Invention

The present invention relates to the field of automatic testing of active plates for liquid crystal displays.

2. Prior Art

LCD panels typically are formed with a liquid crystal material sandwiched between an active plate and a ground plate. Polarizers, colorizing filters and spacers may also be included between the plates. During fabrication, many active panels may be formed on a single glass plate. In each area of the glass plate that is to form an active panel, pixel areas, drive lines, gate lines and drive elements are formed. Typically, thin-film transistors are used for the drive elements.

Because of the relative complexity of the active plate in comparison to the ground plate, most LCD display defects may be traced to some form of defect in the active plate. Because of the substantial additional expense to fabricate operative LCD displays from the active plates, various techniques have been developed for inspecting the active plates alone so that defective active plates can be identified and repaired or discarded at that stage of the fabrication process.

Figure 1:
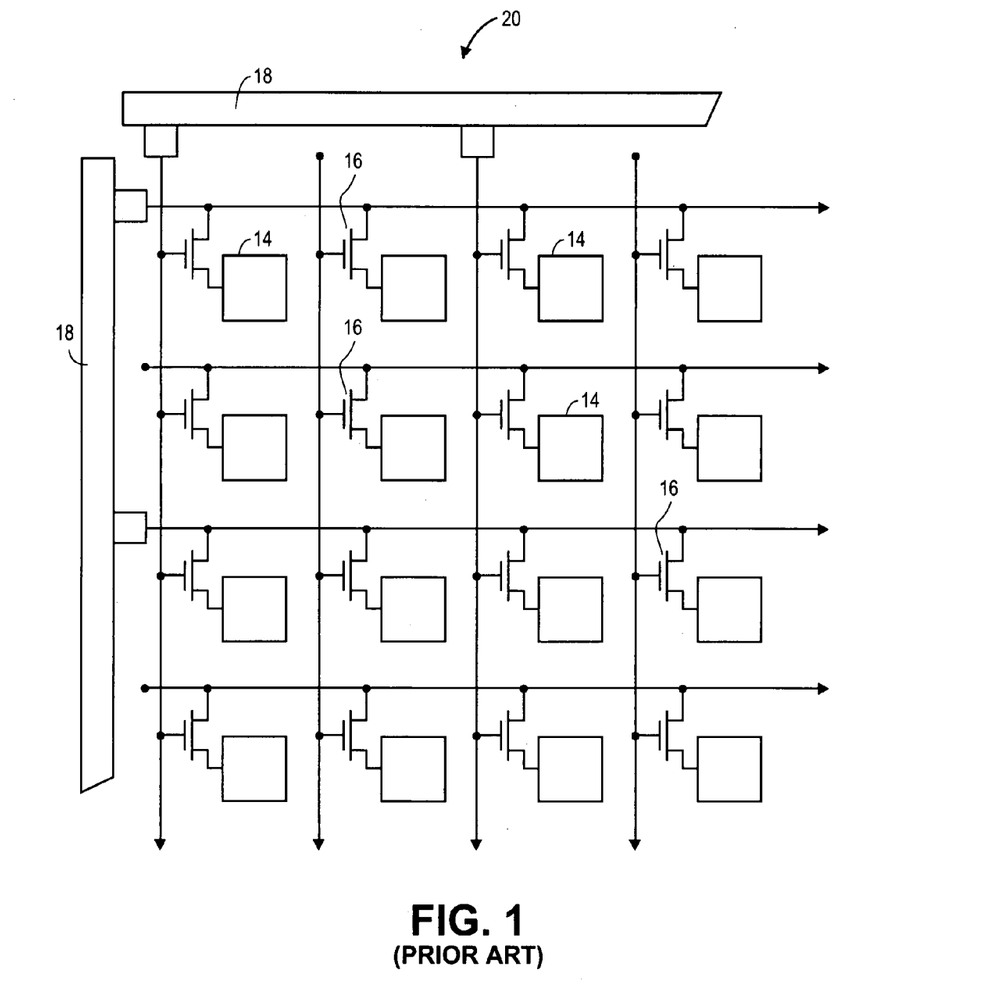
FIG. 1 is an illustration of a portion of an exemplary active plate for a monochrome display.

An exemplary portion of an active plate 20 for a monochrome display is schematically illustrated in FIG. 1. As may be seen therein, a plurality of conductive areas 14 are arranged in an XY matrix, each conductive area defining a pixel in the final display. Associated with each conductive area is a thin film transistor 16 having its input terminal connected to a respective row line in the matrix, and its control terminal or gate connected to a respective column line. In the particular matrix shown in FIG. 1, adjacent row lines are coupled to opposite sides of the matrix, and adjacent column lines are coupled to the top and bottom of the matrix, respectively. A color display may be similar, though each pixel of the display is comprised of 3 pixels on the active plate, each for a different color.

In operation, each conductive area is charged to a voltage on the respective array lines when the respective thin film transistor is turned on by the voltage on the respective column line during each scan of the array. However, while the active plate may be electrically exercised without the ground plate and the liquid crystal material there between, no visibly perceivable changes occur during that exercise.

Various techniques are well known in the prior art for inspecting and testing LCD active plates before proceeding with the further fabrication of the full LCD panel. Each of these techniques is well suited to the detection of certain faults, but not suited to the detection of certain other faults.

One inspection technique that is commonly used is inspection under a visible light using a digital camera and computer based image analysis. Because the active plate is comprised of an array of a large number of pixel areas and thin film transistors, one convenient form of optical inspection is to form a difference image between repetitive patterns in the image. This is commonly called Automatic Optical Inspection (AOI). Without defects, the difference image is zero. With defects, the difference image is positive or negative. In this way, various faults may be detected such as shorts and opens and other faults in geometry that would cause failure of the display to operate, or unacceptable variations in the image intensity across the pixel array. However, other potential faults are not detectable in this manner, such as some faults which cause one or more transistors to not operate properly and/or which prevent pixel conductive areas from maintaining a charge until refreshed on the next scan.

Visible light systems may be either transmissive or pass through (the illumination and camera being on opposite sides of the plate), or reflective (camera and lighting on the same side of the plate), with the active plate fixed and the camera on a transport system for step and repeat operation, particularly with a lighting system moving with the camera to assure uniform lighting for each camera view. Normally the camera is also provided with the Z axis transport system for greater flexibility.

Other known systems for evaluating active plates at that stage of the LCD fabrication process comprise methods of electrically testing the active plate to enable accept/reject decisions based on reasonably accurate projections on how the plate will perform in the finished LCD display. One such technique utilizes a voltage imaging sensor, such as that described in U.S. Pat. No. 4,983,911, assigned to Photon Dynamics, Inc., assignee of the present invention. These systems provide a two-dimensional image of the voltage distribution across a surface of the active plate, thereby allowing the image to be digitized by an appropriate camera. The systems illuminate the active plate with a collimated beam of optical energy of known polarization through an electro-optic modulator disposed sufficiently close to the plate so as to be affected by the voltages on the active plate. Thus the voltage imaging sensor simulates the top half of the LCD panel and converts charge (voltage) on the active plate to visible light. Accordingly, such a system requires at least the electro-optic modulator to be positioned very close to the substrate. This approach can detect faults in operation, such as defective transistors, but has a resolution limit higher than an AOI system.

Systems of the voltage imaging type are manufactured by Photon Dynamics, Inc., assignee of the present invention. Such systems may be plate scale in size or smaller, normally with a camera operating in a step and repeat mode. Both reflective and pass-through systems are known, though normally the reflective mode is used.

Another well known testing technique is the electron beam scanning or e-beam scanning technique. In these testing systems, the active plate is placed in a vacuum chamber and the plate scanned with an electron beam, with the secondary electrons being detected by a scintillation camera. The camera output versus electron-beam position provides the image data for the plate voltage. Typically, a small part of the active plate is scanned at any one time, with the entire plate being scanned in a step and repeat process. Insufficient secondary electrons are indicative of a plate defect.

Finally, active plate testing systems based on charge sensing are also known. These systems are based on the concept of turning on each transistor on the active plate to charge the respective pixel conductive area to a specific voltage, then turning the transistor off, and then turning the transistor on again to short the pixel conductive area to ground while measuring the charge returned from the conductive pixel area. An insufficient charge is indicative of a plate defect. Typically, the transistor on periods while charging the pixel conductive area is on the order of the time the transistor would be on for such purpose in the completed display, and the time before shorting out the pixel conductive area for charge measurement is on the order of the time between scans in the completed LCD.

Thus, in an AOI system using visible light, the camera is typically spaced substantially away from the active plate being inspected, whereas in the voltage imaging sensor type systems, at least the electro-optic modulator must be positioned very close to the active plate to obtain a voltage image of a useful resolution. In an electron beam system, a vacuum environment must be provided, though a camera for providing a two-dimensional image is not required. Instead, only a light sensor is needed, preferably with a photomultiplier to increase the light intensity, with the XY information for a two-dimensional image being provided by the electron beam scan control system. Finally, in the charge sensing type equipment, no camera at all is used, and no mechanical transport system is required beyond that used for loading and unloading the active plate to be tested, such as generally also needed in some form for all of the other testing and inspection systems.

BRIEF SUMMARY OF THE INVENTION

Integrated inspection and test systems for liquid crystal display (LCD) active plates are disclosed. The integrated inspection and test systems may combine visual imaging inspection and an electronic sensing such as voltage imaging, electron beam sensing or charge sensing in a single system, in which the defect information obtained by the visual inspection system is combined with the defect information obtained by the electronic sensing system to produce a defect report. One or more high-resolution visual cameras are scanned over a stationary plate, and the image data from the camera(s) is processed to detect potential defects. A high-resolution electronic sensing system examines the stationary plate, and the image data from the sensor(s) is processed to detect potential defects. The potential defects from the visual image data and electronic sensing image data are processed to produce the final defect information.

DETAILED DESCRIPTION OF THE PREFERRED EMBODIMENTS

In the description to follow, various embodiments of the present invention are disclosed. These various embodiments represent various integrations of inspection and test technologies in a single inspection and test system, as opposed to separate systems for each such technology as are known in the prior art. However, certain design details of the systems of the present invention may be substantially the same or arbitrary and obvious modifications of these individual systems as are known in the prior art. Consequently such details will only be described in a general sense. Other details, particularly those unique to the present invention, will be described at some length to enable one of reasonable skill in the art to make and use the invention.

Figure 2:
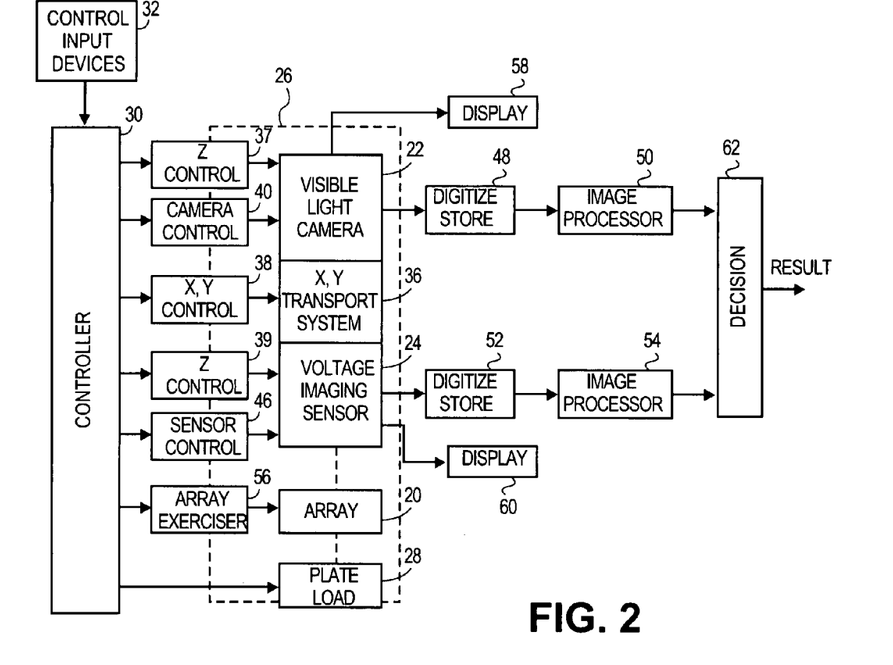
FIG. 2 is a block diagram of a control system for an exemplary integrated inspection and test system using a visible light camera and a voltage imaging sensor.
Figure 3:
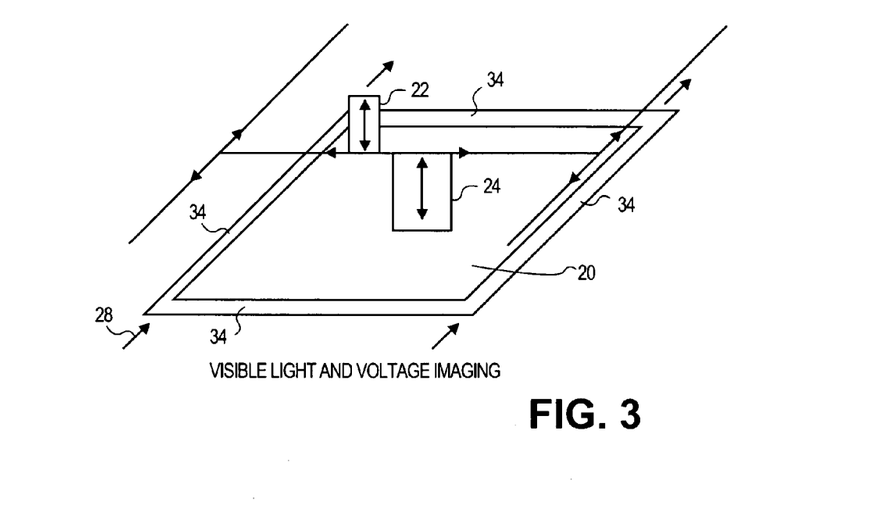
FIG. 3 is a schematic illustration of a transport system for the exemplary system of FIG. 2.

Now referring to FIGS. 2 and 3, a block diagram of a control system for an exemplary integrated inspection and test system and a schematic illustration of a transport system for such a system may be seen, respectively. This system provides visual inspection by way of a visible light camera 22, and voltage imaging testing by a voltage imaging sensor 24. Preferably, the active plate 20 is presented on and loaded into position in the enclosure 26 of the integrated inspection and test system by a robotic system, generally indicated by the numeral 28. The robotic system may be manually controlled, or alternatively, preferably is controlled by a controller 30, which controller controls various other systems of the exemplary embodiment of the present invention. The controller itself will receive various control inputs from control input devices 32, which will include switches, such as manually controlled switches, switches indicative of an active plate being properly loaded, of a further active plate in position for loading, etc., as well as typically a keyboard and control display for menu driven or point-and-click graphical control, or both, as desired.

The loading system used with this embodiment of the present invention, more specifically the plate locating apparatus within the inspection system, includes a system of electrical contacts, generally indicated by the numeral 34, for automatically making contact with contact regions around the periphery of the active plate 20. In general, the plate may be electrically tested with the shorting bars 18 (FIG. 1) in place (see U.S. Pat. No. 5,081,687, the disclosure of which is incorporated herein by reference), or alternatively, contact made with terminal regions of the row and column lines on the active plate and tested accordingly. In general, such transport systems and systems for making contact with the periphery of the active plate are well known in the art, including systems manufactured by Photon Dynamics, Inc., assignee of the present invention.

As may be seen in FIGS. 2 and 3, the visible light camera 22 and the voltage imaging sensor 24 are both supported on an XY transport system, generally indicated by the numeral 36, which is controlled by controller 30 through an XY control system 38. The visible light camera automatic control along the Z axis by Z control 37, as well as the voltage imaging sensor automatic control along the Z axis by Z control 39, are optional and not always required, as manual Z axis adjustments may be made as part of the setup procedure for the inspection and test of active panels of a specific design. The control of motion in the XY plane is preferably through any of the well known X and Y linear transport systems, though other transport systems capable of sweeping out an area such as a rectangular area may be used, such as by way of example, a rho-theta transport system. An XY transport system is preferred however, as being more directly applicable to the step and repeat imaging inspection techniques commonly used in active plate inspection.

The visible light camera is also controlled in functions such as image acquisition, zoom and the like through a camera control 40, also controlled by controller 30. Similarly, the voltage imaging sensor functions are controlled by control 46, also controlled by controller 30.

In general, the visible light camera testing procedures are well known in the prior art. The output of the visible light camera will be digitized and stored (block 48), with image processor 50 providing the image analysis of the images taken. Both the digitizing and storing and the image processing will in general be controlled by controller 30 to be synchronized with the motion of the transport system and operation of the camera. Similarly, the voltage imaging sensor 24 will provide images which are digitized and stored in block 52 and analyzed by image processor 54, the same also being synchronized by controller 30 as the active plate array is exercised by array exerciser 56 providing the control voltages to the array. In general, displays 58 and 60 will be provided to allow viewing of the visible light images and the voltage images, respectively. Alternatively, a single display may be provided, preferably coupled to be able to display the visible light image or the voltage image, or even both images side by side or scaled and overlayed as desired. Ultimately, a pass/fail decision is made and a report provides (block 62) based on the results of the processing of the two images.

Figure 4:
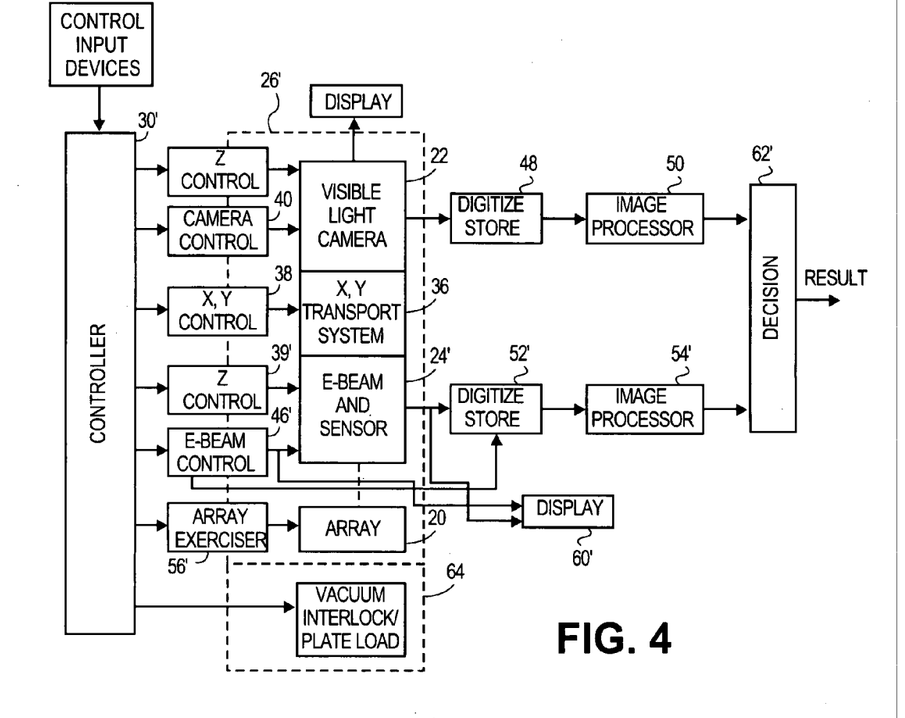
FIG. 4 is a block diagram of a control system for an exemplary integrated inspection and test system using a visible light camera and an electron beam test system.
Figure 5:
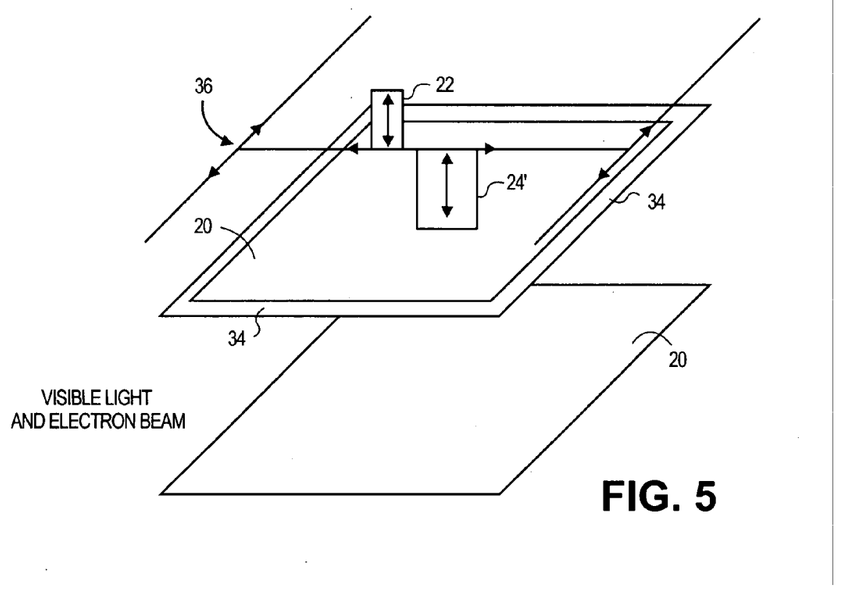
FIG. 5 is a schematic illustration of a transport system for the exemplary system of FIG. 4.

Now referring to FIGS. 4 and 5, another exemplary embodiment of the present invention may be seen. In this embodiment, a visible light inspection system is combined with an electron beam test system. The XY control 38 (FIG. 4), the Z control 37, the XY transport system 36, the plate contacts 34, the camera control 40, the visible light camera 22, the digitize and store circuit 48, the display 58, and the image processor 50 may be identical or substantially the same as that used in the prior embodiment.

With respect to the enclosure for the inspection and test system of this embodiment, a vacuum environment is required for the electron beam and sensor 24'. Accordingly, the enclosure 26' in this embodiment is a vacuum enclosure that may be pumped down to a vacuum range characteristic of prior art e-beam test equipment. Also, as is characteristic in the prior art in e-beam test equipment, a second vacuum interlock and plate load chamber 64 is provided. The vacuum chamber 64 is a small, simple chamber which may be vented for loading and unloading of the active plates, yet readily quickly evacuated to the required vacuum levels so that an active plate to be tested may be transferred from the vacuum chamber 64 to the main enclosure 26', and an inspected active plate may be transferred from the main enclosure 26' to the vacuum interlock 64 without venting the main vacuum chamber 26'. This avoids having to repeatedly pump down the larger vacuum enclosure 26', and equipment therein which may be slow to release air trapped therein. While not shown, a second vacuum chamber may be used if desired so that during the testing of one plate, both interlock chambers may be vented, one to release the plate previously tested and one to receive the next plate to be tested, after which both are pumped down to the required vacuum, one to receive the plate being inspected and tested when completed, and the other to immediately thereafter load the next plate to be inspected and tested.

As with the voltage imaging sensor of FIGS. 2 and 3, the electron beam testing of the active array 20 proceeds with voltages on the array being controlled by the array exerciser 56' controlled by controller 30'. The electron beam control 46' controls the sweep of the electron beam across the surface of the active plate and provides information as to the beam position to digitize and store (Block 52') the output of the sensor and to provide sweep information for the display 60'. Image processor 54' is used to analyze the electron beam image information, with the results of the inspection and testing being provided, together with the output of the visual image processor 50, to a decision making module 62' to provide a final inspection and test report. The electron beam generator and sensor 24' may be controlled in Z position by the Z axis control 39', though as before, the Z axis control may be a manual control or adjustment made as part of the initial setup for the inspection and test of active plates of a particular design.

Figure 6:
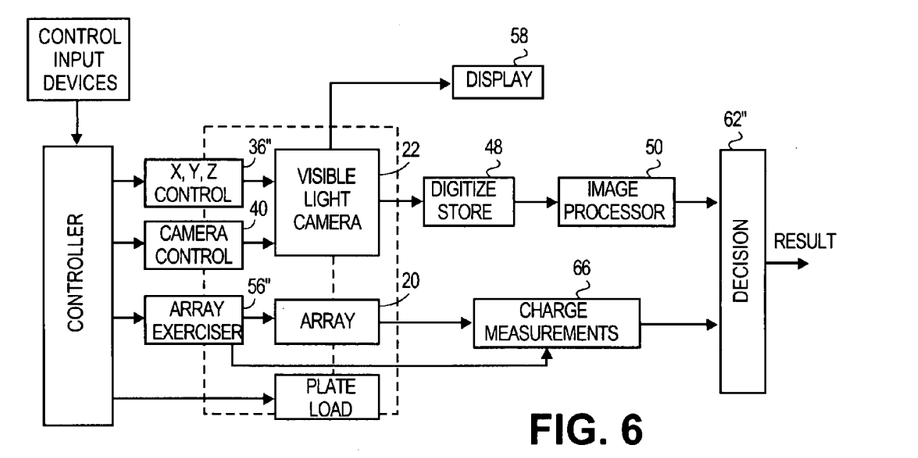
FIG. 6 is a block diagram of a control system for an exemplary integrated inspection and test system using a visible light camera and a charge sensing system.
Figure 7:
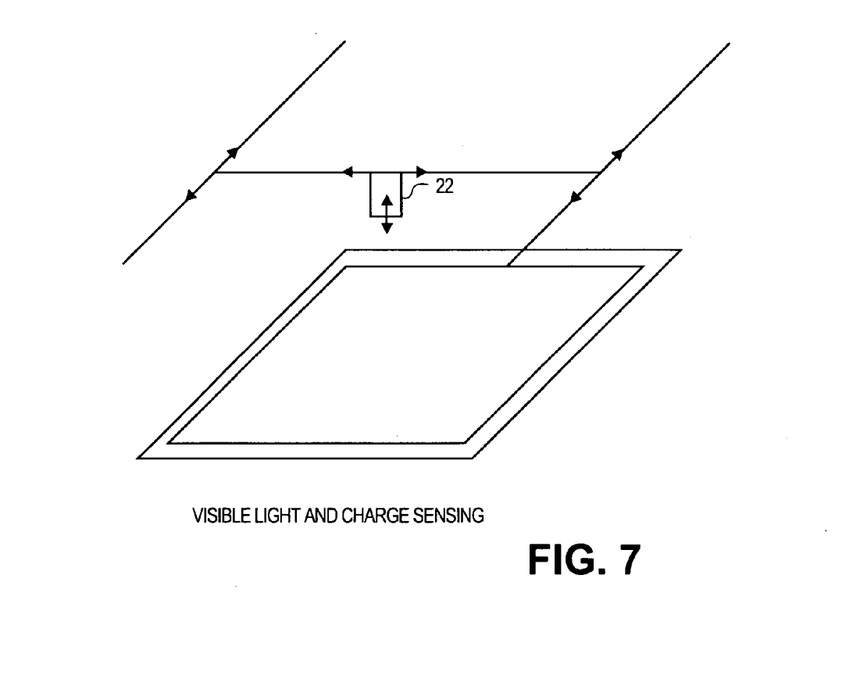
FIG. 7 is a schematic illustration of a transport system for the exemplary system of FIG. 6.

Now referring to FIGS. 6 and 7, a block diagram of a control system for a further exemplary integrated inspection and test system and a schematic illustration of a transport system for such a system, specifically a system which combines inspection by way of a visible light camera and testing of the array by charge sensing may be seen. In this system, since the testing by charge sensing is totally electronic, transport system 36" is only needed for the visible light camera 22. In the embodiment of FIGS. 6 and 7, the plate load system may be the same as that used in the embodiment of FIGS. 2 and 3, with the array 20 being electrically exercised by the array exerciser 56" and the charge measurements made in block 66 and results provided to the decision module 62" to provide the inspection and test report.

The visible light camera inspection systems and the voltage imaging sensing system disclosed herein have been disclosed in the context of reflective systems, though pass-through systems are also known in the art. In a visible light camera pass-through system, for instance, the light source and the visible light camera are on opposite sides of the active plate. Similarly, in a pass-through type voltage imaging system, the source of polarized light and the camera are on opposite sides of the active plate (see for instance U.S. Pat. No. 4,983,911 assigned to Photon Dynamics, Inc. assignee of the present invention). While such systems are not preferred, in part because of the greater complexity of the transport system required, either or both the visual image inspection system and the voltage imaging system used with the present invention could be of the pass-through type if desired.

The control systems disclosed in FIGS. 2, 4, and 6 are of course exemplary only. In general, the various functions identified therein or variations thereof may be carried out under program control using one or more processors as desired. Also, while the inspection and test systems disclosed herein have in general been disclosed with respect to independently processing the information obtained from the inspection (visible light) system and the applicable electrical test system, the digitization and analysis of the images may be done by sharing the computer equipment required by the multiple systems. Also one of the advantages of the present invention is the ability to simultaneously have access to the inspection and the testing information, which can have a considerable diagnostic value for accept/reject, repair/scrap decisions and process control purposes.

While one of the advantages of the preferred embodiments of the present invention is the economy of the sharing of a single transport system by multiple sensors, multiple transport systems may be used if desired. This still preserves the economies of shared electronics, enclosures and the like, of reduced floor space in comparison to separate systems, and the advantages of reduced plate handling and of having combined inspection and test results while the plate remains in the system. There are, however, certain restraints caused by the integration of two transport systems within a single station or assembly. One of the restraints is the physical restraint that the visible light camera and the voltage imaging sensor or electron beam source and sensor and the respective transport systems do not collide with each other. In general, the voltage imaging sensor and electron beam sensor will be positioned close to the surface of the active plate, whereas the visible light camera 22 will normally be positioned substantially above the surface of the active plate. Consequently, the visible light camera transport system may readily be positioned sufficiently above the voltage imaging sensor/electron beam sensor transport system so that the XY transport systems can readily be configured to not ever collide. However, it is possible with a Z axis control on the visible camera 22 that the camera, particularly when in a lower position, could collide with the voltage imaging sensor. In this case, the controller must be programmed to lift the visible image camera vertically out of the way whenever the visible light camera and the voltage imaging sensor are to be brought within a pre-determined proximity of each. This restriction is fairly easily accommodated in software by those of reasonable skill in the art, though one might choose to design the transport systems so that in the event of some failure causing a collision, the two transport systems would hang up without damaging each other, or alternatively one would overpower the other without damaging the same. As a further alternate, if simultaneous visible light inspection and voltage imaging sensing/electron beam sensing is not to be done, the voltage imaging sensor/electron beam sensor may have a park position beyond one edge of the active plate to be inspected and the visible light camera have its own park position beyond an edge of the active plate to be inspected so that each one may separately scan the active plate while the other is in the park position, thereby preventing any possibility of collision. It does have the disadvantage however of negating the possibility of simultaneous inspection using the two inspection technologies.

Another restraint is the optical restraint namely the restraint of not obstructing the view of the visible light camera by the voltage image sensor/electron beam sensor or any part of its transport system. This too is easily accommodated in software if simultaneous operation of the two systems is contemplated, or if not, may be entirely avoided by having park positions beyond the edges of the active plate being inspected as previously described.

There has been described herein certain specific embodiments of the present invention. However the disclosed embodiments are exemplary only, as the present invention may be practiced in ways too numerous to each be individually disclosed in detail herein. Thus, while certain preferred embodiments of the present invention have been disclosed, it will be obvious to those skilled in the art that various changes in form and detail may be made therein without departing from the spirit and scope of the invention.

What is claimed is:

1. Apparatus for inspecting an active plate for a liquid crystal display, the active plate having a matrix of active elements coupled to row and column lines on a first of first and second sides of the active plate, comprising:

within a single station having an inspection function and a test function, a holder adapted to hold an active plate and to make electrical contact to the row and column lines on the first side of the active plate, a visual image camera positioned to provide visual image data for an active plate in the holder, and an electronic sensor disposed adjacent the first side of the active plate adapted to sense operation of the active plate;

a processor electrically coupled to the holder to electrically couple to an active plate in the holder and electrically exercise an active plate in the holder;

a visual image processor coupled to the visual image camera receiving the visual image data for an active plate in the holder and processing the visual image data for the detection of faults on the active plate; and, an electronic sensor output processor electrically coupled to the electronic sensor to process the output of the electronic sensor to detect faults during the electrical operation of the active plate.

2. The apparatus of claim 1 wherein the electronic sensor comprises a voltage image sensor.

3. The apparatus of claim 1 wherein the inspection station comprises a first vacuum chamber and the electronic sensor comprises an e-beam sensor.

4. The apparatus of claim 3 wherein the inspection station further comprises a second vacuum chamber coupled to the first vacuum chamber for loading and unloading active plates into and out of the holder in the first vacuum chamber.

5. The apparatus of claim 1 wherein the visual image camera is mounted on a visual image transport system for movement of the visual image camera about an area parallel to an active plate in the holder.

6. The apparatus of claim 5 wherein the visual image transport system includes visual camera motion in a direction perpendicular to an active plate in the holder.

7. The apparatus of claim 1 wherein the electronic sensor is mounted on an electronic sensor transport system for movement of the electronic sensor about an area parallel to an active plate in the holder.

8. The apparatus of claim 1 wherein the visual image camera is mounted on a visual image transport system for movement of the visual image camera about an area parallel to an active plate in the holder, and the electronic sensor is mounted on an electronic sensor transport system for movement of the electronic sensor about an area parallel to an active plate in the holder, the electronic sensor transport system being disposed between an active plate in the holder and the visual image transport system.

9. Apparatus for inspecting an active plate for a liquid crystal display, the active plate having a matrix of active elements coupled to row and column lines on a first of first and second sides of the active plate, comprising:

within a single station having an inspection function and a test function, a holder adapted to hold an active plate and to make electrical contact to the row and column lines on the first side of the active plate, a visual image camera positioned to provide visual image data for an active plate in the holder, and an electronic sensor disposed adjacent the first side of the active plate adapted to sense operation of the active plate;

a processor electrically coupled to the holder to electrically couple to an active plate in the holder and electrically exercise an active plate in the holder;

a visual image processor coupled to the visual image camera receiving the visual image data for an active plate in the holder and processing the visual image data for the detection of faults on the active plate; and, an electronic sensor output processor electrically coupled to the electronic sensor to process the output of the electronic sensor to detect faults during the electrical operation of the active plate;

the visual image camera being mounted on a visual image transport system for movement of the visual image camera about an area parallel to an active plate in the holder, and the electronic sensor being mounted on an electronic sensor transport system for movement of the electronic sensor about an area parallel to an active plate in the holder, the electronic sensor transport system being disposed between an active plate in the holder and the visual image transport system; and, a controller coupled to the visual image camera, the visual image transport system, the electronic sensor and the electronic sensor transport system to provide simultaneous scanning of the active plate by the visual image camera and the electronic sensor in a step and repeat process without the transport systems mechanically interfering with each other and without the electronic sensor interfering with the visual images of the active plate processed by the visual image processor.

10. Apparatus for inspecting an active plate for a liquid crystal display, the active plate having a matrix of active elements coupled to row and column lines on a first of first and second sides of the active plate, comprising:
within a single station having an inspection function and a test function, a holder adapted to hold an active plate and to make electrical contact to the row and column lines on the first side of the active plate, and a visual image camera providing visual image data for an active plate in the holder;
a processor electrically coupled to the holder to electrically couple to an active plate in the holder and for each transistor in a matrix on the active plate, to charge, and to thereafter discharge that transistor to measure the charge retained on the active plate prior to discharge for detection of electrical faults in the active plate; and,
a visual image processor coupled to the visual image camera receiving the visual image data for an active plate in the holder and processing the visual image data for the detection of visual faults in the active plate.

11. The apparatus of claim 10 wherein the visual image camera is mounted on a visual image transport system for movement of the visual image camera about an area parallel to an active plate in the holder.

12. The apparatus of claim 11 wherein the visual image transport system includes visual camera motion in a direction perpendicular to an active plate in the holder.

13. A method of inspecting and testing an active plate having a matrix of active elements coupled to row and column lines on a first of first and second sides of the active plate, comprising:
positioning an active plate within a single station having an inspection function and a test function;
making electrical contact to the row and column lines on the first side of the active plate to exercise the active elements on the plate;
inspecting the active plate with a visual image camera for detection of visually perceivable faults on the active plate; and,
inspecting the active plate with an electronic sensor adapted to sense faults during the electrical operation of the active plate.

14. The method of claim 13 wherein inspecting the active plate with an electronic sensor comprises inspecting the active plate with a voltage image sensor.

15. The method of claim 14 further comprised of loading and unloading active plates into and out of the inspection station through a second vacuum environment.

16. The method of claim 13 wherein positioning an active plate within an inspection station comprises positioning an active plate in a vacuum environment within an inspection station, and inspecting the active plate with an electronic sensor comprises inspecting the active plate with an e-beam sensor.

17. The method of claim 13 wherein inspecting the active plate with a visual camera comprises inspecting the active plate with a visual camera by moving the visual image camera about an area parallel to an active plate in the holder in a step and repeat pattern.

18. The method of claim 17 wherein inspecting the active plate with a visual camera includes motion of the visual camera in a direction perpendicular to an active plate in the holder.

19. The method of claim 13 wherein inspecting the active plate with an electronic sensor comprises inspecting the active plate with an electronic sensor by moving the electronic sensor about an area parallel to an active plate in the holder in a step and repeat pattern.

20. The method of claim 13 wherein inspecting the active plate with a visual camera comprises inspecting the active plate with a visual camera by moving the visual image camera about an area parallel to an active plate in the holder in a step and repeat pattern, and inspecting the active plate with an electronic sensor comprises inspecting the active plate with an electronic sensor by moving the electronic sensor about an area parallel to an active plate in the holder in a step and repeat pattern.

21. The method of claim 13 wherein inspecting the active plate with an electronic sensor comprises charging each transistor in a matrix on an active plate and thereafter discharging that transistor to measure the charge retained on the active plate prior to discharge for detection of electrical faults in the active plate.

22. A method of inspecting and testing an active plate having a matrix of active elements coupled to row and column lines on a first of first and second sides of the active plate, comprising:
positioning an active plate within a single station having an inspection function and a test function;
making electrical contact to the row and column lines on the first side of the active plate to electrically exercise the active elements on the plate;
inspecting the active plate with a visual image camera for detection of visually perceivable faults; wherein inspecting the active plate with a visual camera includes inspecting the active plate with a visual camera by moving the visual image camera about an area parallel to an active plate in the holder in a step and repeat pattern, and testing the active plate with an electronic sensor by moving the electronic sensor about an area parallel to an active plate in the holder in a step and repeat pattern;
inspecting the active plate with an electronic sensor adapted to sense faults in the operation of the active plate while electrically exercising the active elements on the active plate; and,
controlling the visual image camera and the electronic sensor to provide simultaneous scanning of the active plate by the visual image camera and the electronic sensor in a step and repeat process without mechanically interfering with each other and without the electronic sensor interfering with the visual images of the visual image camera.

* * * * *